United States Patent
Patterson et al.

(10) Patent No.: US 10,799,598 B2
(45) Date of Patent: Oct. 13, 2020

(54) DISULFIDE BRIDGING CONJUGATES

(71) Applicant: Sorrento Therapeutics, Inc., San Diego, CA (US)

(72) Inventors: James T. Patterson, San Diego, CA (US); Gunnar F. Kaufmann, San Diego, CA (US); Yanwen Fu, San Diego, CA (US); Tong Zhu, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 46 days.

(21) Appl. No.: 16/052,406

(22) Filed: Aug. 1, 2018

(65) Prior Publication Data

US 2019/0038764 A1 Feb. 7, 2019

Related U.S. Application Data

(60) Provisional application No. 62/539,850, filed on Aug. 1, 2017.

(51) Int. Cl.
*A61K 47/68* (2017.01)
*A61K 47/55* (2017.01)

(52) U.S. Cl.
CPC .......... *A61K 47/6851* (2017.08); *A61K 47/55* (2017.08); *A61K 47/6849* (2017.08)

(58) Field of Classification Search
CPC . A61K 47/6851; A61K 47/6849; A61K 47/55
See application file for complete search history.

(56) References Cited

U.S. PATENT DOCUMENTS

| | | | |
|---|---|---|---|
| 10,301,395 | B2 | 5/2019 | Fu et al. |
| 2015/0105539 | A1 | 4/2015 | Mia et al. |
| 2016/0326266 | A1 | 11/2016 | Fu et al. |
| 2017/0137539 | A1 | 5/2017 | Fu et al. |

OTHER PUBLICATIONS

Sausville et al. (Cancer Research, 2006, vol. 66, pp. 3351-3354) (Year: 2006).*
Johnson et al. (British J. of Cancer, 2001, 84(10):1424-1431) (Year: 2001).*
Tai et al (Prostate. Nov. 2011; 71(15): 1668-1679) (Year: 2011).*
Chames, P. et al., "Bispecific antibodies for cancer therapy: the light at the end of the tunnel?" MAbs. Nov.-Dec. 2009; 1(6): 539-547.
Wang, et al., "Targeted treatment of prostate cancer," J. Cell. Biochem. 2007, 102, 571-579.

(Continued)

*Primary Examiner* — Angela C Brown-Pettigrew
(74) *Attorney, Agent, or Firm* — McNeill Baur PLLC

(57) ABSTRACT

Provided are bispecific conjugates having the general formula:

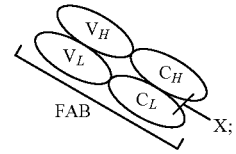

pharmaceutically acceptable salts thereof, pharmaceutical compositions thereof, and their use in the treatment of cancer.

18 Claims, 5 Drawing Sheets

(56) References Cited

OTHER PUBLICATIONS

Kim et al., "Bispecific small molecule—antibody conjugate targeting prostate cancer, Proceedings of the National Academy of Sciences," vol. 10, No. 44, Oct. 29, 2013, pp. 17796-17801.
Hull et al., "Homogeneous Bispecifics by Disulfide Bridging," American Chemical Society, Bioconjugate Chemistry, Jul. 17, 2014, pp. 1395-1401.
Ramadoss et al., "An Anti-B Cell Maturation Antigen Bispecific Antibody for Multiple Myeloma," Journal of the American Chemical Society, Apr. 29, 2015, vol. 137, pp. 5288-5291.

* cited by examiner

DISULFIDE BRIDGING CONJUGATES

RELATED APPLICATIONS

This application claims the benefit of priority of U.S. Provisional Application No. 62/539,850, filed on Aug. 1, 2017, the entire contents of which are incorporated by reference in its entirety herein.

BACKGROUND

Cancer is, and still remains, the leading cause of death worldwide. According to the American Cancer Society, the average lifetime risk of developing cancer for American males is 40.8%, or a little less than one in two. Prostate cancer is most predominant cancer in males and is the second leading cause of death. While traditional approaches for treating cancer have had success, these approaches are often plagued by the lack of targeted treatments, drug resistance, and specialized problems associated with particular strains. For example, oesophageal, prostate, and pancreatic cancer are extremely difficult to treat because they are often slow growing, remain symptom free, and metastasize.

Bispecific antibodies or conjugates have emerged as useful therapeutic tools to selectively target cancers. In these instances, one portion of the conjugate is affixed a motif that is responsible for binding a target cell and a second portion is affixed with a synthetic agent such as a drug, protein, cytotoxin, polymer, or nanoparticle. Clinical successes and impressive treatment profiles for bispecific conjugates have been shown. See e.g., MAbs. 2009 November-December; 1(6): 539-547.

Prostate-specific antigen (PSMA) is overexpressed in most prostate cancer cells, but is present at low or undetectable levels in normal cell. Studies have revealed that PSMA is the second most upregulated protein in prostate cancer and that expression levels rise depending upon the severity of the cancer. See e.g., Wang, et al., J. Cell. Biochem. 2007, 102, 571-579). These distinctions provide a unique opportunity for selective targeting PSMA. Taken together with bispecific conjugates, simultaneously targeting PSMA and presenting T-cell surface antigen (CD3) provides a new generation of selective cancer targeting drugs.

SUMMARY

Provided herein are bispecific conjugates having the general formula:

In these conjugates, the fragment antigen binding (FAB) fragment of an antibody is chemically bonded to a targeting moiety X through disulfide bonds on the constant heavy ($C_H$) and constant light (CO chains of the FAB fragment. Compositions comprising these bispecific conjugates and their use for the treatment of one or more cancers are also provided.

The bispecific conjugates and compositions described herein can be manufactured in commercially relevant yields and quantities, utilize digestions on off-the-shelf antibodies or cells (e.g., CHO cells), undergo facile conjugation processes, and elicit the exclusive formation of heterodimers (with high assembly yield). These processes mitigate conventional requirements for extensive protein engineering, complex genetic techniques, and laborious biochemical processing.

DETAILED DESCRIPTION

1. General Description of Conjugates

In one embodiment, provided herein are bispecific conjugates having the formula:

or a pharmaceutically acceptable salt thereof, wherein FAB represents the fragment antigen binding fragment of an antibody; $V_L$, $V_H$, $C_L$, and $C_H$ represent the variable light, variable heavy, constant light, and constant heavy portions of the FAB fragment; the bond between $C_L$ and $C_H$ represents a disulfide bond, and is the point to which a chemical targeting group X is attached.

2. Definitions

The term "small molecule" means an non-peptide organic compound having a molecular weight of less than 900 daltons and which elicits a biological response in a subject. Small molecules include e.g., lipids, monosacchirides, second messengers, natural products, and metabolites.

The term "peptide" refers to compounds which are short chains of amino acid monomers linked by amide bonds.

The term "protein" means a large biomolecule or macromolecule comprising one or more long chains of amino acid residues. Proteins may be made up of naturally occurring amino acids and peptide bonds, or synthetic peptidomimetic structures. "Amino acid" means both naturally occurring and synthetic amino acids. For example, homo-phenylalanine, citrulline and norleucine are considered amino acids. "Amino acid" also includes imino acid residues such as proline and hydroxyproline. The side chains may be in either the (R) or (S) configuration. Proteins include antibodies.

The term "nucleic acid" means at least two nucleotides covalently linked together. A nucleic acid generally contains phosphodiester bonds, although in some cases, nucleic acid analogs are included that may have alternate backbones, comprising, for example, phosphoramide. Mixtures of naturally occurring nucleic acids and analogs are contemplated. The nucleic acids may be single stranded or double stranded, or contain portions of both double stranded or single stranded sequence. The nucleic acid may be DNA, both genomic and cDNA, RNA or a hybrid, where the nucleic acid contains a combination of deoxyribo- and ribo-nucleotides. Nucleic acids may naturally occurring nucleic acids, random nucleic acids, or "biased" random nucleic acids. For example, digests of prokaryotic or eukaryotic genomes may be used. Where the ultimate expression product is a nucleic acid, at least 10, at least 12, at least 15, or at least 21 nucleotide positions need to be randomized.

As used herein, the term "polymer" refers to a large molecule or marcromolecule comprised of many repeated subunits.

The term "nanoparticle" refers to a particle that is between 1 and 100 nanometers in size.

Chemical targeting groups which can be used in the present compounds include, but are not limited to, bombesin; auristatins such as MMAE and MMAF; maytansinoids such as DM1 and DM4; inhibitors of MDMX, MDM2, MDMX/MDM2, STAT3, and KRAS; compounds that bind avb3 integrin, compounds that bind a gastrin releasing peptide receptor, compounds that bind neurokinin 1 receptor, compounds that bind melanocortin 1 receptor, compounds that bind neuropeptide Y receptor Erlotinib (TARCEVA®, Genentech/OSI Pharm.), Bortezomib (VELCADE®, Millennium Pharm.), Fulvestrant (FASLODEX®, Astrazeneca), Sutent (SU11248, Pfizer), Letrozole (FEMARA®, Novartis), Imatinib mesylate (GLEEVECO, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNEO, Wyeth), Lapatinib (GSK572016, GlaxoSmithKline), Lonafarnib (SCH 66336), Sorafenib (BAY43-9006, Bayer Labs.), and Gefitinib (IRESSA®, Astrazeneca), AG1478, AG1571 (SU 5271; Sugen), alkylating agents such as Thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gammal I and calicheamicin omegall (Angew Chem Intl. Ed. Engl. (1994) 36 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, anthramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCINO doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINEO vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; tamoxifen (including NOLVADEX® tamoxifen), raloxifene, droloxifene, 4-hydroxytamoxifen, trioxifene, keoxifene, LY117018, onapristone, and FARESTON toremifene; (ii) aromatase inhibitors that inhibit the enzyme aromatase, which regulates estrogen production in the adrenal glands, such as, for example, 4(5)-imidazoles, aminoglutethimide, MEGASE® megestrol acetate, AROMASINO exemestane, formestanie, fadrozole, RIVISOR® vorozole, FEMARA® letrozole, and ARIMIDEX® anastrozole; (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those which inhibit expression of genes in signaling pathways implicated in abherant cell proliferation, such as, for example, PKC-alpha, Ralf and H-Ras; (viii) ribozymes such as a VEGF expression inhibitor (e.g., ANGIOZYME® ribozyme) and a HER2 expression inhibitor; (ix) vaccines such as gene therapy vaccines, for example, ALLOVECTINO vaccine, LEUVECTINO vaccine, and VAXID® vaccine; PROLEUKINO rIL-2; LURTOTECAN® topoisomerase 1 inhibitor; ABARELIX® rmRH; and (x) anti-angiogenic agents such as bevacizumab (AVASTINO, Genentech).

Other targeting groups include, but are not limited to mycophenolate mofetil such as CELLCEPT®; azathioprine (IMURAN®, AZASAN®/6-mercaptopurine; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids and glucocorticosteroids, e.g., prednisone, prednisolone such as PEDIAPRED® (prednisolone sodium phosphate) or ORAPRED® (prednisolone sodium phosphate oral solution), methylprednisolone, and dexamethasone; methotrexate (oral or subcutaneous) (RHEUMATREX®, TREXALL™); hydroxycloroquine/chloroquine; sulfasalazine; leflunomide; cytokine or cytokine receptor antagonists including anti-interferon-y, -13, or -a antibodies, anti-tumor necrosis factor-a antibodies (infliximab or adalimumab), anti-TNFa immunoadhesin (ENBREL®, etanercept), anti-tumor necrosis factor-I3 antibodies, anti-interleukin-2 antibodies and anti-IL-2 receptor antibodies; anti-LFA-1 antibodies, including anti-CD11 a and anti-CD18 antibodies; anti-L3T4 antibodies; heterologous anti-lymphocyte globulin; polyclonal or pan-T antibodies, or monoclonal anti-CD3 or anti-CD4/CD4a antibodies; soluble peptide containing a LFA-3 binding domain (WO 90/08187); streptokinase; TGF-β; streptodornase; RNA or DNA from the host; FK506; RS-61443; deoxyspergualin; rapamycin; T-cell receptor (Cohen et al., U.S. Pat. No. 5,114,721); T-cell receptor fragments (Ofiher et al. Science 251: 430-432 (1991); WO 90/11294; Ianeway, Nature 341:482 (1989); and WO 91/01133); T cell receptor antibodies (EP 340,109) such as T 1 OB9; cyclophosphamide (CYTOXAN®); and dapsone; penicillamine.

The term "antibody" includes monoclonal antibodies, polyclonal antibodies, multispecific antibodies (including bispecific antibodies), antibody fragments that can bind an antigen (including, Fab', F'(ab)$_2$, Fv, single chain antibodies, diabodies), and recombinant peptides comprising the foregoing as long as they exhibit the desired biological activity and antigen binding specificity. In one embodiment, an antibody is a full length or intact antibody. A full length antibody comprises four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments, the FRs of the antibody may be identical to the human germline sequences, or may be naturally or artificially modified.

The disclosed conjugates may exist in various stereoisomeric forms. Stereoisomers are compounds that differ only in their spatial arrangement. Diastereomers are stereoisomers that contain two or more asymmetrically substituted carbon atoms.

When the stereochemistry of a disclosed conjugate is named or depicted by structure, it is to be understood that one of the encompassed stereoisomers or any mixture of the encompassed stereoisomers are included. It is to be further understood that the stereoisomeric purity of the named or depicted stereoisomer is at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed conjugate is named or depicted by structure without indicating the stereochemistry, it is to be understood that the name or structure encompasses one stereoisomer free of other stereoisomers, mixtures of stereoisomers, or mixtures of stereoisomers in which one or more stereoisomers is enriched relative to the other stereoisomer(s). For example, the name or structure may encompass one stereoisomer free of other diastereomers, mixtures of stereoisomers, or mixtures of stereoisomers in which one or more diastereomers is enriched relative to the other diastereomer(s).

Pharmaceutically acceptable salts of the conjugates herein are contemplated. For use in medicines, the salts of the conjugates described herein refer to non-toxic "pharmaceutically acceptable salts." Pharmaceutically acceptable salt forms include pharmaceutically acceptable acidic/anionic or basic/cationic salts.

The term "pharmaceutically acceptable carrier" refers to a non-toxic carrier, adjuvant, or vehicle that does not destroy the pharmacological activity of the conjugate with which it is formulated. Pharmaceutically acceptable carriers, adjuvants or vehicles that may be used in the compositions of this disclosure include, but are not limited to, organic or inorganic carriers, excipients or diluents suitable for pharmaceutical applications.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to reduce the likelihood of recurrence or to delay the recurrence.

The term "effective amount" as used herein, refers to an amount of a conjugate disclosed herein, which is sufficient to effect treatment of a disease when administered to a subject. A therapeutically effective amount will vary depending upon the relative activity of the conjugate and depending upon the subject and disease condition being treated, the weight and age of the subject, the severity of the disease condition, the manner of administration and the like, which can readily be determined by one of ordinary skill in the art.

3. Description of Exemplary Conjugates

In a first embodiment, provided herein are bispecific conjugates having the formula:

or a pharmaceutically acceptable salt thereof, wherein FAB represents the fragment antigen binding fragment of an antibody; $V_L$, $V_H$, $C_L$, and $C_H$ represent the variable light, variable heavy, constant light, and constant heavy portions of the FAB fragment; the bond between $C_L$ and $C_H$ represents a disulfide bond, and is the point to which a chemical targeting group X is attached; and the targeting group X is selected from a protein, nanoparticle, polymer, nucleic acid, peptide, or small molecule. In one aspect, X is a small molecule or protein. In another aspect, X is a small molecule.

In a second embodiment, the bispecific conjugates described herein are of the Formula:

or a pharmaceutically acceptable salt thereof, wherein each n is independently an integer from 2 to 20; each m is independently an integer from 2 to 15; and the hashed bonds indicate the points of attachment to the FAB fragment.

In a third embodiment, n is independently an integer from 2 to 16, wherein the remaining variables are as described above in the second embodiment. In another alternative, n is independently an integer from 2 to 12, wherein the remaining variables are as described above in the second embodiment. In another alternative, n is independently an integer from 2 to 10, wherein the remaining variables are as described above in the second embodiment. In another alternative, n is independently an integer from 2 to 12, wherein the remaining variables are as described above in the second embodiment. In yet another alternative, n is independently an integer from 4 to 8. In yet another aspect, n is 8, wherein the remaining variables are as described above in the second embodiment.

In a fourth embodiment, m is independently an integer from 2 to 14, wherein the remaining variables are as described above in the second or third embodiment. In another alternative, m is independently an integer from 2 to 12, wherein the remaining variables are as described above in the second or third embodiment. In another alternative, m is independently an integer from 2 to 10, wherein the remaining variables are as described above in the second or third embodiment. In another alternative, m is independently an integer from 4 to 10, wherein the remaining variables are as described above in the second or third embodiment. In yet another alternative, m is independently an integer from 4 to 8, wherein the remaining variables are as described above in the second or third embodiment. In yet another aspect, m is 6, wherein the remaining variables are as described above in the second or third embodiment.

(I)

; or (II)

;

In a fifth embodiment, the bispecific conjugates described herein are of the Formula:

or a pharmaceutically acceptable salt thereof.

4. Uses, Formulation and Administration

In certain embodiments, the present disclosure provides a method of treating a patient (e.g., a human) with a cancer comprising the step of administering to the patient an effective amount of a conjugate described herein, or a pharmaceutically acceptable salt or composition thereof.

Examples of cancers treated using the conjugates and methods described herein include, but are not limited to, adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, actue promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In one aspect the diseases and conditions treatable by the according to the methods using the bispecific antibody compounds described herein are selected from non-Hodgkin lymphoma (NHL), prostate cancer, B-cell lymphoma, acite myeloid leukemia (AML), colon cancer, and breast cancer. In one embodiment, the bispecific antibody compounds described herein are used as bispecific T cell engagers, and are able to exert action on its antigen selectively and direct the human immune system to act against a tumor cell.

In one embodiment, a subject is treated with a conjugate described herein and a pharmaceutically acceptable carrier, adjuvant, or vehicle, wherein said conjugate is present in an amount to treat or ameliorate one or more of the diseases and conditions recited above. In an alternative embodiment, the cancers by a conjugate described herein include, any one of those described above. In one aspect, the cancers are selected from non-Hodgkin lymphoma (NHL), prostate cancer, B-cell lymphoma, acite myeloid leukemia (AML), colon cancer, breast cancer, in the patient.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The term "pharmaceutically acceptable carrier" refers to a non-toxic carrier, adjuvant, or vehicle that does not destroy the pharmacological activity of the antibody with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided bispecific antibody compound in the composition will also depend upon the particular compound in the composition.

EXEMPLIFICATION

As depicted in the Examples below, conjugates are prepared according to the following general procedures. It will be appreciated that, although the general methods depict the synthesis of certain compounds herein, the following general methods, and other methods known to one of ordinary skill in the art, can be applied to all conjugates described herein.

Preparation of FAB from IgG1

Proteolytic digestion of IgG1 allowed generation of Fab. SpeB cysteine protease, FabULOUS (Genovis), was used to digest the hinge region of IgG1 to produce Fab and Fc fragments. A digestion procedure was adopted using 0.1-0.15 U/µg enzyme overnight (~16 h) at 37° C. in a buffer containing 20 mM imidazole, 0.5 M NaCl, and 20 mM sodium phosphate (pH 7.4) with 0.1 mM dithiothreitol (DTT). Fab purification was enabled by tandem HisTrap FF (GE) and HiTrap MabSelect SuRe (GE) purification on an ÄKTA Pure FPLC system. His-tagged protease was removed by the Ni-sepharose column, while digested Fc fragment and any undigested IgG1 was retained in the Protein A column. Fab was collected in the flow-through fractions and buffer exchanged into DPBS or 20 mM sodium phosphate buffer pH 7.4. Fab purity was then assessed by standard methods.

Bioconjugation Reaction

αCD3 Fab conjugate was prepared through reduction of the interchain disulfide bonds followed by conjugation with dibromo-functionalized linker containing the 2-[3-(1,3-dicarboxypropyl)ureido]pentanedioic acid (DUPA) targeting moiety. Fab (5 mg/mL) was typically reduced using 10 or 20 equivalents of DTT in 20 mM sodium phosphate buffer (pH 7.4) for 1 h at RT. Reducing agent was removed by Sephadex G-25 (GE) gravity column and buffer exchange into 20 mM sodium phosphate buffer with 5 mM diethylenetriaminepentaacetic acid (DTPA) (pH 7.4). Next, conjugation with 10 equivalents DUPA linker in buffer containing 7.5% organic co-solvent proceeded overnight at RT. Excess linker was removed by centrifugal filtration using Amicon Ultra 10 kDa NMWL units (Millipore). This method was used to afford conjugates of Formula 1 and 2. See Scheme 1 below.

Scheme 1:

The Hydrophobic Interaction Chromatography and Mass Spectrum analysis for the aCD3 Fab and the product, the conjugate of Formula 1 are shown in FIGS. 2A and 2B, and FIGS. 3A and 3B, respectively.

SDS-PAGE Analysis

Sodium dodecyl sulfate polyacrylamide gel electrophoresis (SDS-PAGE) was employed using NuPAGE Novex 4-12% Bis-Tris Protein Gels with NuPAGE MOPS SDS Running Buffer in a XCell SureLock Mini electrophoresis system. All samples (2 μg) included NuPAGE LDS Sample Buffer and were heated to 70° C. for 5 min prior to loading. Reduced samples also contained NuPAGE Sample Reducing Agent. Mark12 Unstained Standard (10 μL) was used for estimation of molecular weights. After gel electrophoresis at 125 V for 1.5 h, gels were fixed for 5 min and stained with SYPRO Ruby Protein Gel Stain following the recommended procedures. Imaging was performed with a Bio-Rad Chemi-Doc MP System and analyzed by Image Lab Software. Heavy chain-light chain disulfide bridging was determined to be ~85% efficient.

Hydrophobic Interaction Chromatography (HIC) HPLC

Analysis by HIC HPLC used a TOSOH TSKgel Butyl-NPR (4.6 mm ID×10 cm, 2.5 μm) column at 40° C. on an Agilent 1260 Infinity system. Analytical runs were performed using 50 μg sample with a linear gradient of 0-60% B over 30 min: A=50 mM sodium phosphate+1 M ammonium sulfate (pH 7), B=50 mM sodium phosphate+25% isopropanol (pH 7). All data was analyzed using OpenLAB Software. HIC HPLC of αCD3 Fab conjugation with dibromomaleimide-PEG8-DUPA shows a major product (~80%) corresponding to the addition of a single linker while only a minor peak of doubly conjugated Fab was produced.

LCMS Analysis of Intact Protein

For intact MS analysis, 5 μg aCD3 Fab or aCD3 Fab conjugate was injected onto an Agilent PLRP-S (1000 Å, 5 μm, 2.1×50 mm) column at 80° C. Antibody was eluted from the column with an 8 min gradient (25-60% B, 0.5 mL/min flow rate). Mobile phase A was 0.1% formic acid in water, and mobile phase B was 0.1% formic acid in acetonitrile.

All experiments were performed on a Waters H class UPLC system coupled to a Waters Xevo G2 TOF mass spectrometer. The mass spectrometer was operated in positive ion, sensitivity mode with detection in the range of 500-4000 m/z. Source parameters were as follows: capillary voltage, 3.0 kV; sampling cone voltage, 40.0 V; source temperature, 125° C.; desolvation temperature, 350° C.; cone gas flow, 10 L/hr; desolvation gas flow, 800 L/hr. The protein peak was deconvolved by MassLynx MaxEnt1 function according to the following parameters: output resolution, 2.0 Da/channel; uniform Gaussian width at half height, 0.8 Da for intact antibody; minimum intensity ratios 10% for left and right; maximum number of iteration of 12.

LCMS demonstrated a rather homogeneous preparation of aCD3 Fab from enzymatic digestion. Reduction and conjugation of Fab with dibromomaleimide-PEG8-DUPA linker resulted in the major conjugated product containing a single linker bridging the inter-chain disulfide bond.

Luminescence Cytotoxicity Assay with Fab

Firefly luciferase transduced prostate cancer target cell lines were used for cytotoxicity assays, LNCaP (ATCC® CRL-1740™), PSMA+(cultured in RPMI-1640+10% non-heat-inactivated FBS+0.5 μg/mL Puromycin) and PC-3 (ATCC® CRL-1435™), PSMA-(cultured in RPMI-1640+ 10% heat-inactivated FBS+1.0 μg/mL Puromycin). Cells were harvested with TrypLE (ThermoFisher Scientific) then resuspended in fresh RPMI-1640+10% heat-inactivated FBS and plated at 4,000 cells/well in 100 μL. After overnight incubation at 37° C. in a humidified 5% $CO_2$ incubator, serial dilutions of proteins in RPMI-1640+10% heat-inactivated medium (50 μL) were added to the assay plates at the indicated concentrations. In experiments utilizing effector cells, freshly thawed peripheral blood mononuclear cells (PBMCs) were washed with media and added to the assay plates at 40,000 cells in 50 μL to obtain an effector:target ratio of 10:1. After 4 days incubation, 90 μL was removed from assay plates and 90 μL ONE Glo Luciferase Assay Reagent (Promega # E6120) was mixed with the samples and incubated at room temperature for 10 min. Samples were transferred to white 96-well flat bottom plates for luminescence measurements using a PerkinElmer EnSpire multimode plate reader. Data was analyzed using GraphPad Prism software.

Figure 1:
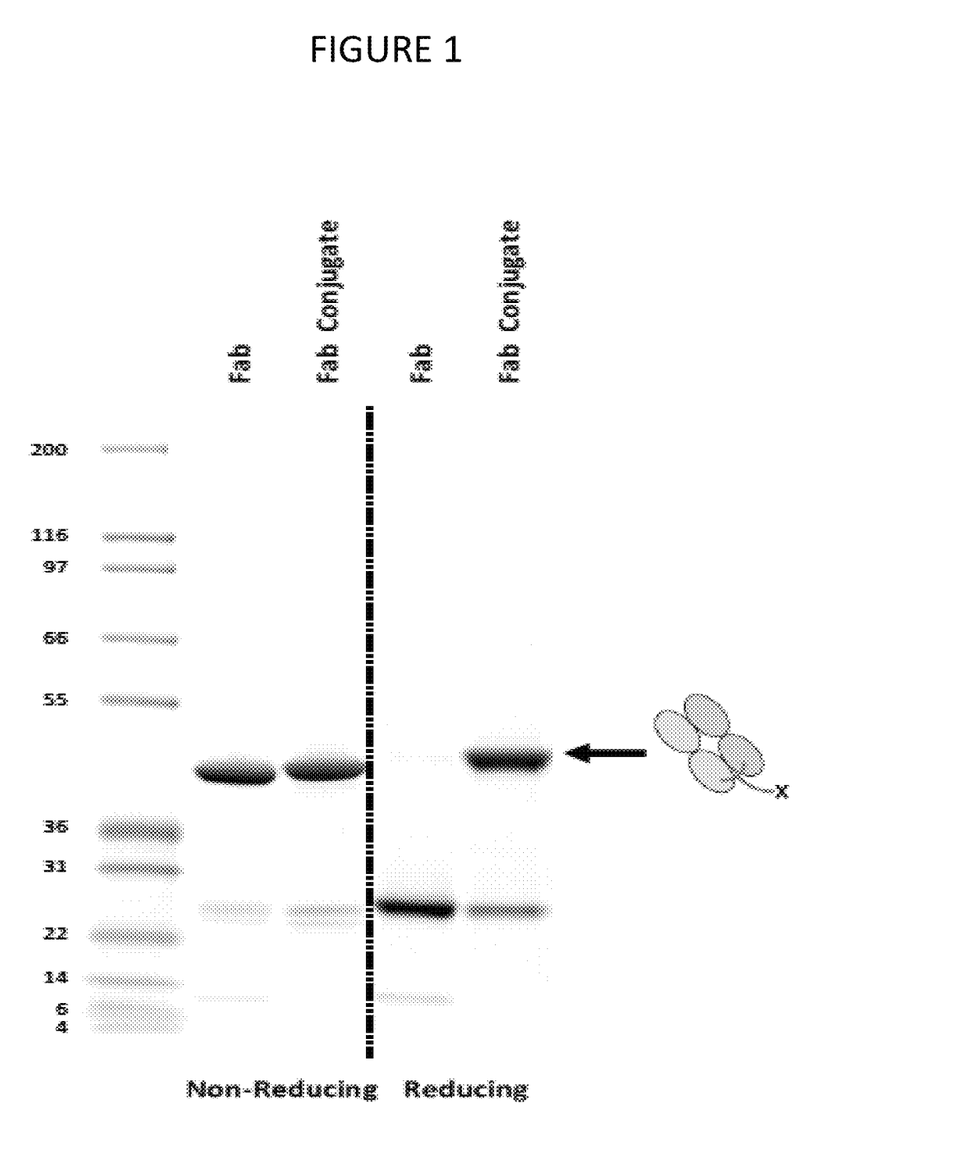
FIG. 1 illustrates an SDS-PAGE gel analysis of intermediates involved in the synthesis of an exemplary bispecific antibody.
Figure 2A:
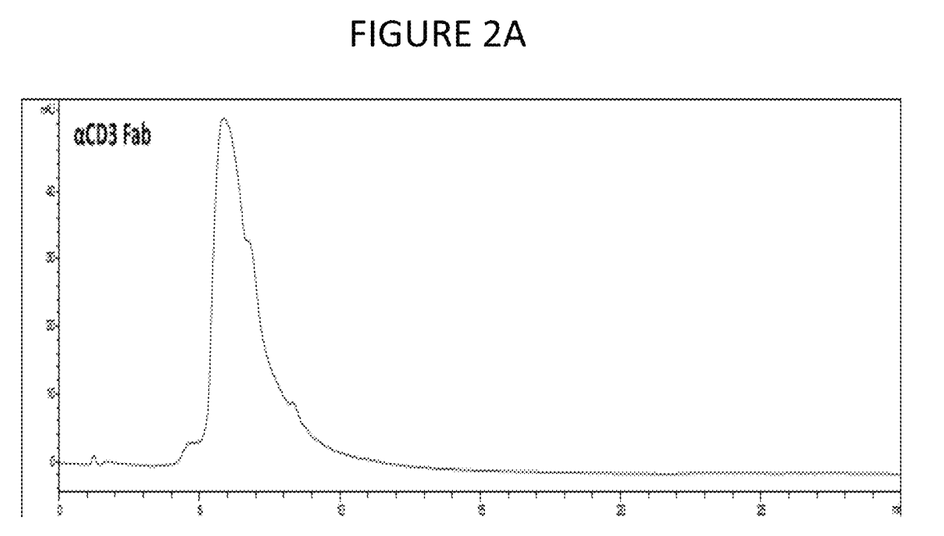
FIG. 2A and FIG. 2B illustrate a Hydrophobic Interaction Chromatography (HIC) analysis of the aCD3 Fab (2A) and the conjugate having the Formula 1 (2B).
Figure 2B:
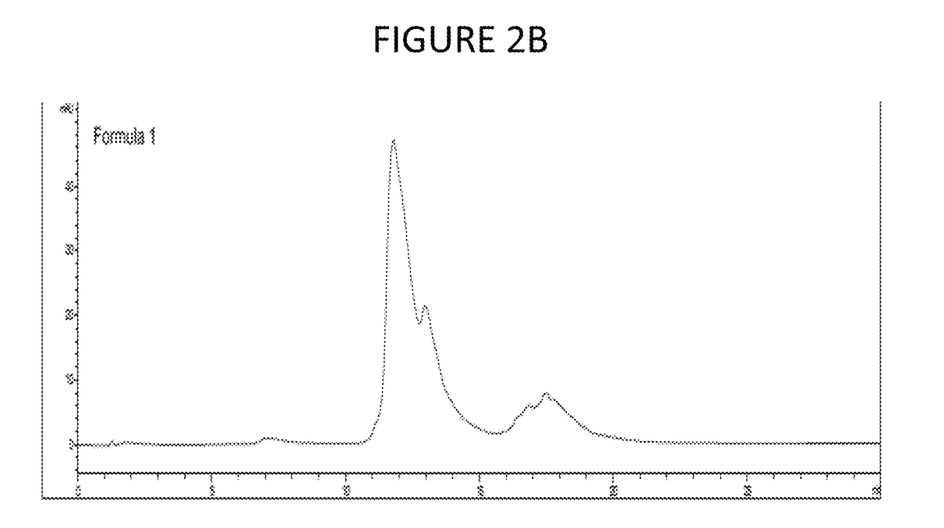
Figure 3A:
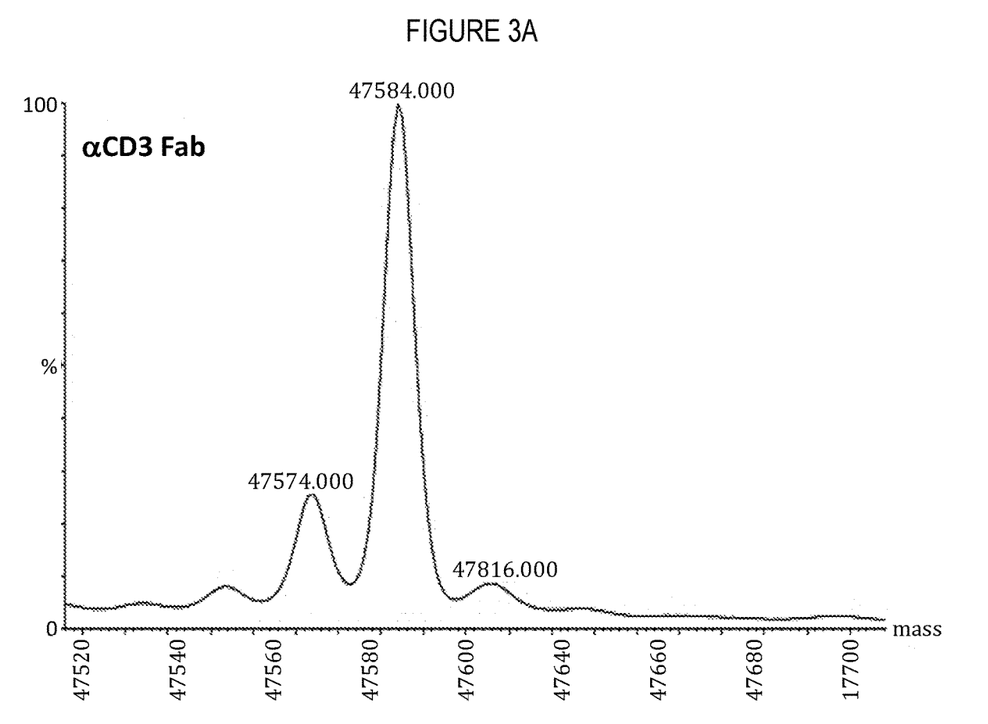
FIG. 3A and FIG. 3B illustrate a mass spectrum analysis for the aCD3 Fab (3A) the conjugate having the Formula 1 (3B).
Figure 3B:
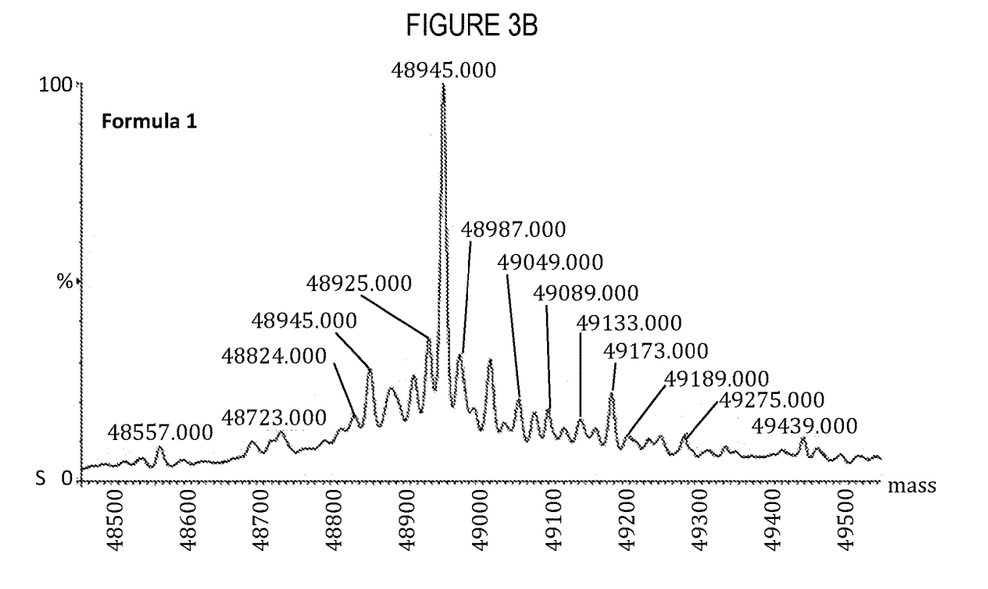
Figure 4A:
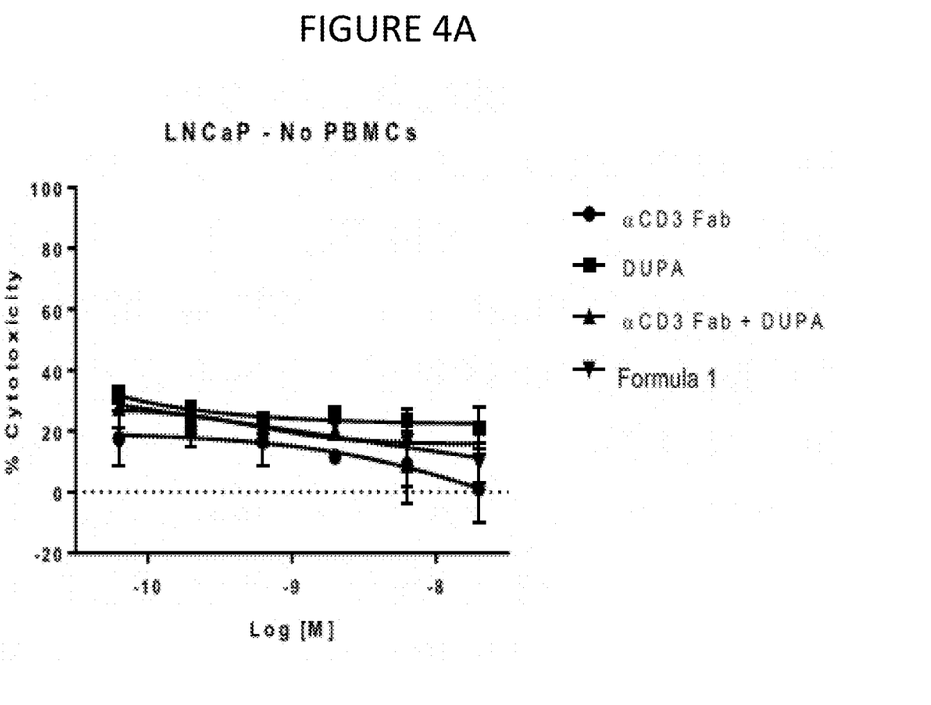
FIG. 4A and FIG. 4B show the cytotoxicity of LNCap (4A) and PC-3 cells (4B) absent PSMA treated with controls and the conjugate having the Formula 1.
Figure 4B:
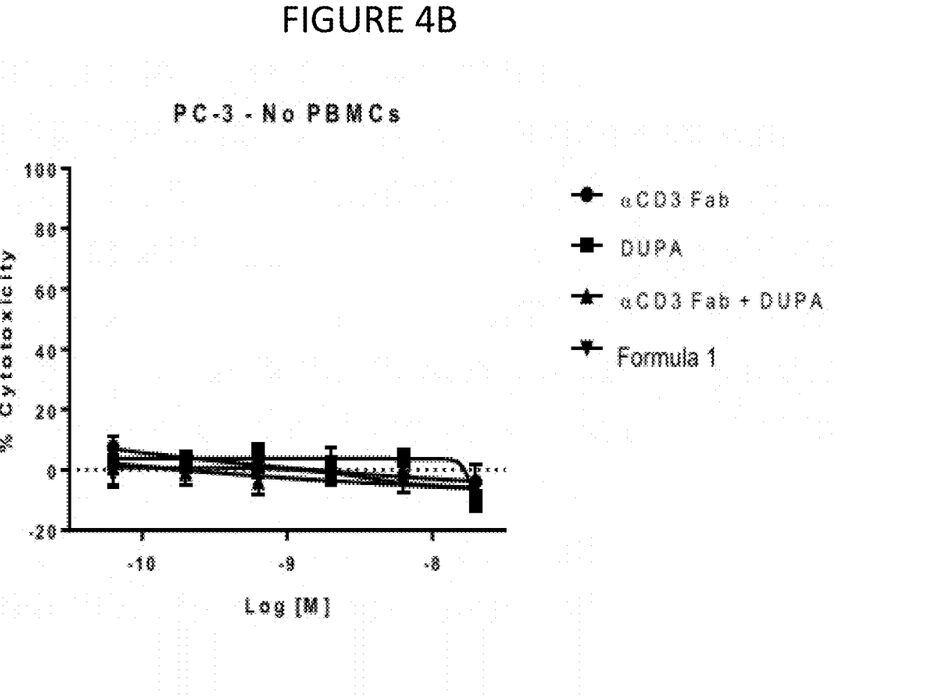
Figure 5A:
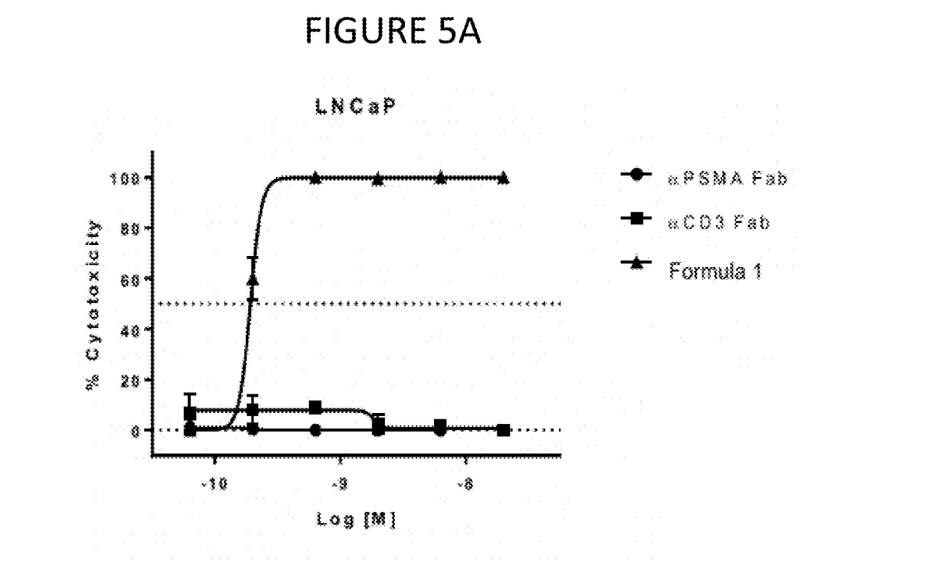
FIG. 5A and FIG. 5B show the cytotoxicity of LNCap (5A) and PC-3 cells (5B) with PSMA treated with controls and the conjugate having the Formula 1.
Figure 5B:
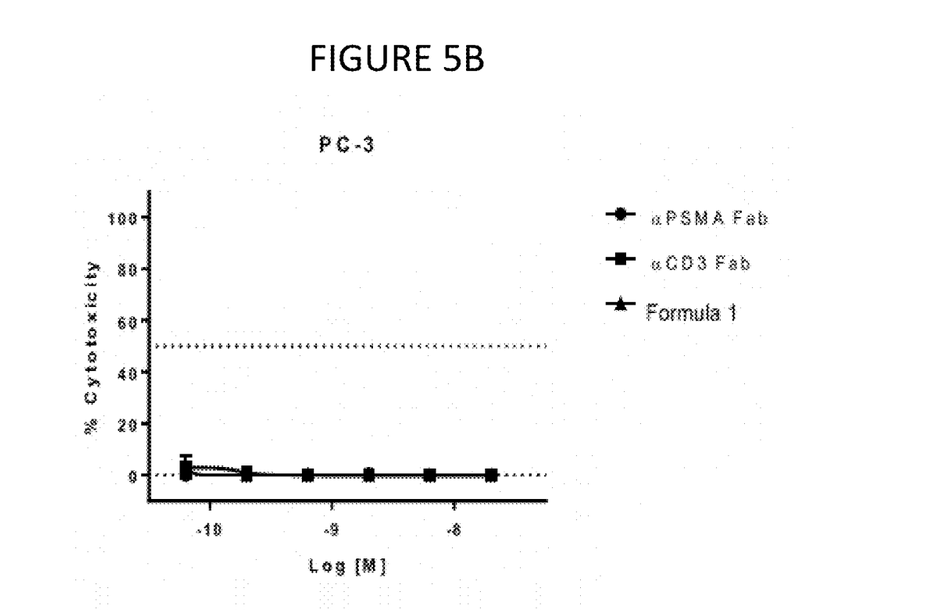

Cell killing was analyzed in the absence of effector cells (FIGS. 4A and 4B) to monitor any inherent cytotoxic activities of aCD3 Fab, DUPA small molecule, the combination of Fab and small molecule, and aCD3-DUPA conjugate. No dose-dependent cell killing activity was observed up to 20 nM for any of the tested samples, independent of the presence (LNCaP) or absence (PC-3) of PSMA antigen expression.

αPSMA and αCD3 Fabs did not show cytotoxic activity in the presence of PMBCs (FIGS. 5A and 5B). However, cell killing of LNCaP cells but not PC-3 cells was evident with aCD3-DUPA. The data indicate that potent PSMA-directed cytotoxicity (190 pM) with conjugated Fab was achieved using PBMC effector cells.

While we have described a number of embodiments, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. An antibody Fab conjugate having a Formula I or a Formula II:

Formula I

Formula II or a pharmaceutically acceptable salt thereof, wherein each n is independently an integer from 2 to 20; each m is independently an integer from 2 to 15; and wherein each FAB fragment is connected to a pyrrolidine-dione moiety or a $CH_2$-quinoxalinyl moiety through native cysteine residues in the Fab fragment.

2. The antibody Fab conjugate of claim 1, wherein n is an integer from 2 to 12.

3. The antibody Fab conjugate of claim 2, wherein n is an integer from 4 to 10.

4. The antibody Fab conjugate of claim 3, wherein n is 8.

5. The antibody Fab conjugate of claim 1 wherein m is an integer from 2 to 10.

6. The antibody Fab conjugate of claim 5, wherein m is an integer from 4 to 8.

7. The antibody Fab conjugate of any one of claim 6, wherein m is 6.

8. The antibody Fab conjugate of claim 7, wherein the FAB fragment comprises a CD3 binding region.

9. A pharmaceutical composition comprising the antibody Fab conjugate of claim 1, or a pharmaceutically acceptable salt thereof; and a pharmaceutically acceptable carrier.

10. A method of treating prostate cancer or adenocarcinoma, comprising administering to a subject in need thereof a conjugate of claim 1, or a pharmaceutically acceptable salt thereof, or the composition of claim 9.

11. The method of claim 10, wherein the subject has prostate cancer.

12. The method of claim 10, wherein the subject has an adenocarcinoma.

13. A method of inducing cell death of a PSMA-expressing cell, comprising contacting the PSMA-expressing cell with the conjugate of claim 1.

14. The method of claim 13, wherein the FAB fragment comprises a CD3 binding region.

15. The method of claim 13, wherein the conjugate induces cell death in an effector-cell-dependent manner.

16. The method of claim 15, wherein the effector cell is a peripheral blood mononuclear cell.

17. The antibody Fab conjugate of claim 1, which is of Formula I.

18. The antibody Fab conjugate of claim 1, which is of Formula II.

* * * * *